United States Patent [19]
Reenstra

[11] Patent Number: 5,222,391
[45] Date of Patent: Jun. 29, 1993

[54] TENNIS BALL TESTER

[76] Inventor: Arthur L. Reenstra, 5987 Bunch Rd., Summerfield, N.C. 27358

[21] Appl. No.: 741,756

[22] Filed: Aug. 7, 1991

[51] Int. Cl.$^5$ ............................................. G01N 3/48
[52] U.S. Cl. ...................................................... 73/81
[58] Field of Search .................... 73/78, 79, 81, 818, 73/18, 862.68, 765, 4 R, 115; 340/665

[56] References Cited

U.S. PATENT DOCUMENTS

| | | | |
|---|---|---|---|
| 2,278,416 | 4/1942 | Atti | 265/19 |
| 2,626,522 | 1/1953 | Brown | 73/94 |
| 2,628,496 | 2/1953 | Wick | 73/818 |
| 2,703,492 | 3/1955 | Brissette et al. | 73/94 |
| 3,376,734 | 4/1968 | Ether | 73/78 |
| 3,665,757 | 5/1972 | Hoag | 73/94 |
| 4,004,457 | 1/1977 | Eide et al. | 73/818 |
| 4,136,554 | 1/1979 | Larson | 73/81 |
| 4,313,289 | 2/1982 | Birdsong | 53/84 |
| 4,555,028 | 11/1985 | Valehrach | 73/78 |
| 4,586,018 | 4/1986 | Bettman | 73/115 |
| 4,590,808 | 5/1986 | Lightfoot et al. | 73/862.48 |
| 5,062,294 | 11/1991 | Iwata | 73/115 |

FOREIGN PATENT DOCUMENTS 230250  3/1925  United Kingdom .

OTHER PUBLICATIONS

Tech Note entitled "FSR Technical Specifications" 1989.

*Primary Examiner*—Robert Raevis
*Attorney, Agent, or Firm*—Rhodes, Coats & Bennett

[57] ABSTRACT

A device for automatically measuring the compressibility of a tennis ball or the like. The tennis ball tester of the present invention contains three main components: a case to compress the ball to a fixed dimension; a force sensor to measure the force applied to the ball; and an electronic comparative circuit to determine the force level against a standard and to activate a LED indicator for displaying a "go-no go" output. In operation, the ball is first placed in the case and compressed to a fixed dimension by closing the lid of the case. This dimension is the maximum the ball should be compressed by an 18 lb. specified force. As the ball is compressed, the tennis ball tester measures the applied force to determine if the force is less than or greater than the 18 lb. specified force. The force sensor measures this force and supplies an electrical signal proportional to the force measured. The electrical signal is compared by the comparative circuit which activates a red or green LED indicator depending on the force level necessary to compress the ball. Since the force necessary to compress the ball is a measure of the compressibility of the ball, the LED indicators also indicate the playing condition of the ball.

13 Claims, 2 Drawing Sheets

TENNIS BALL TESTER

BACKGROUND OF THE INVENTION

1. Field of the Invention

The present invention relates generally to compression testing machines and, more particularly, to a new and unique compression testing machine for indicating the playing condition of a tennis ball or the like.

2. Description of the Prior Art

The playing condition of a tennis ball or the like is very important to the players. Despite stringent efforts to properly inflate the balls during manufacturing to predetermine degrees of pressure, followed by careful testing and pressure packaging, tennis balls and the like frequently do not have the uniform bounce and other play characteristics required for play, particularly professional play.

The primary characteristic which is necessary to good playing condition is compressibility. Normally, the only way for a player to determine the compressibility of the balls is to squeeze them manually or bounce them. These are not sufficiently accurate methods for gauging the playing condition of the tennis ball. Accordingly, competitive players customarily disregard balls after relatively short intervals of play and open new balls to insure uniform performance during play.

Under American Tennis Association (ATA) rules, a tennis ball should have a rebound of more than 53 inches and less than 58 inches when dropped 100 inches upon a concrete base. Specifically, the ball shall have a forward deformation of more than 0.220 inches and less than 0.290 inches and a return deformation of more than 0.350 inches and less than 0.425 inches at a 18 lb. load.

Under the ATA rules, all deformation tests conducted under Rule 3 shall use a machine designed by Percy Stevens and patented in Great Britain under Patent No. 230,250, the entire specification of which is hereby incorporated by reference. Deformation testing is conducted by placing the ball on the Stevens machine so that neither platen of machine is in contact with the cover seam. The contact weight is then applied and the dials are set to zero. A test weight equivalent to 18 lbs. is placed on the beam and pressure is applied by turning the wheel at uniform speed so that the pointer on the machine is level with the mark to balance the pressure placed on the beam. The amount of deformation caused to the ball is its forward deformation value. It is this value that is the most critical to indicating the condition of the tennis ball. Clearly, such measurements are too complicated and the Stevens device is too cumbersome to be used except for as part of manufacturing quality control and for professional tournament play.

U.S. Pat. No. 4,590,808 issued to Lightfoot discloses a device and method for determining the tension factor of grids such as tennis rackets and the like. The device includes a frame having a fixed predetermined test area including a mechanism for relating two measurement components, a deflection component and a force component; an element for applying a first measurement component to the grid test area; an element for sensing the other component resulting from the application of the first component; and means for determining from the two components a tension factor in the strings forming the grid. The apparatus also includes a mechanism and method for determining the compressibility of balls such as tennis balls.

U.S. Pat. No. 4,313,289 issued to Birdsong discloses a method for manufacturing a tennis ball, racket ball or other gas-filled ball by inflating the ball with air or gas to such a degree that the ball will precisely balance a given force on the ball producing a given deflection on the ball.

U.S. Pat. No. 3,665,757 issued to Hoag discloses a gauge for checking the concentricity and the compression of a golf ball having a lever for moving a first anvil a given distance against the ball, thereby forcing the ball to move against a second anvil which registers the ball compression against a helical spring on a dial gauge. U.S. Pat. No. 2,278,416 issued to Atti discloses a similar type device.

Finally, U.S. Pat. No. 2,703,492 issued to Brissette and U.S. Pat. No. 2,626,522 issued to Brown are examples of devices for measuring the modulus of compression of rubber-like materials.

As can be seen from a review of the these references, none of the prior art devices provide a simple, economical and reliable means for measuring the condition of a tennis ball in a device which is portable and which can be used by a player on the court to provide a "go-no go" indication of the condition of the game ball. Thus, there remains a need for a new and improved tennis ball tester which is simple and economical to operate and which provides a reliable indication of the condition of the tennis ball.

SUMMARY OF THE INVENTION

The present invention is directed to a device for automatically measuring the compressibility of a tennis ball or the like. The tennis ball tester of the present invention contains three main components: a case to compress the ball to a fixed dimension; a force sensor to measure the force applied to the ball; and an electronic comparative circuit to determine the force level against a standard and to activate a LED indicator for displaying a "go-no go" output.

In operation, the ball is first placed in the case and compressed to a fixed dimension by closing the lid of the case. This dimension is the maximum the ball should be compressed by an 18 lb. specified force. As the ball is compressed, the tennis ball tester measures the applied force to determine if the force is less than or greater than the 18 lb. specified force. The force sensor measures this force and supplies an electrical signal proportional to the force measured. The electrical signal is compared by the comparative circuit which activates a red or green LED indicator depending on the force level necessary to compress the ball. Since the force necessary to compress the ball is a measure of the compressibility of the ball, the LED indicators also indicate the playing condition of the ball.

Accordingly, one aspect of the present invention is to provide an apparatus for determining the playing condition of a tennis ball or the like. The apparatus includes: (a) means for compressing the ball to a predetermined dimension; (b) sensor means for sensing the force exerted by the compressed ball and providing a signal representative of the force; and (c) means for receiving the signal representative of the force and comparing the signal to a predetermined value representative of a ball in good playing condition and providing an output signal representative of the condition of the ball.

Another aspect of the present invention is to provide a sensor assembly for an apparatus for determining the playing condition of a tennis ball or the like by compressing the ball to a predetermined dimension and measuring the force necessary to compress the ball to the predetermined position. The apparatus includes: (a) sensor means for sensing the force exerted by the compressed ball and providing a signal representative of the force, wherein the sensor means is a polymeric thick film device which exhibits a decreasing resistance as increasing force is applied normal to the surface of the device and further including means located between the device and the ball for distributing the force exerted by the ball upon the surface of the ball, thereby resulting in improved accuracy of the sensor means; and (b) means for receiving the signal representative of the force and comparing the signal to a predetermined value representative of a ball in good playing condition and providing an output signal representative of the condition of the ball.

Still another aspect of the present invention is to provide an apparatus for determining the playing condition of a tennis ball or the like. The apparatus includes: (a) means for compressing the ball to a predetermined dimension; (b) sensor means for sensing the force exerted by the compressed ball and providing a signal representative of the force wherein the sensor means is a polymeric thick film device which exhibits a decreasing resistance as increasing force is applied normal to the surface of the device; and (c) means for receiving the signal representative of the force and comparing the signal to a predetermined value representative of a ball in good playing condition and providing an output signal representative of the condition of the ball.

These and other aspects of the present invention will become apparent to those skilled in the art after a reading of the following description of the preferred embodiment when considered with the drawings.

DESCRIPTION OF THE PREFERRED EMBODIMENTS

In the following description, like references characters designate like or corresponding parts throughout the several views. Also in the following description, it is to be understood that such terms as "forward", "rearward", "left", "right", "upwardly", "downwardly", and the like are words of convenience and are not to be construed as limiting terms.

Figure 1:
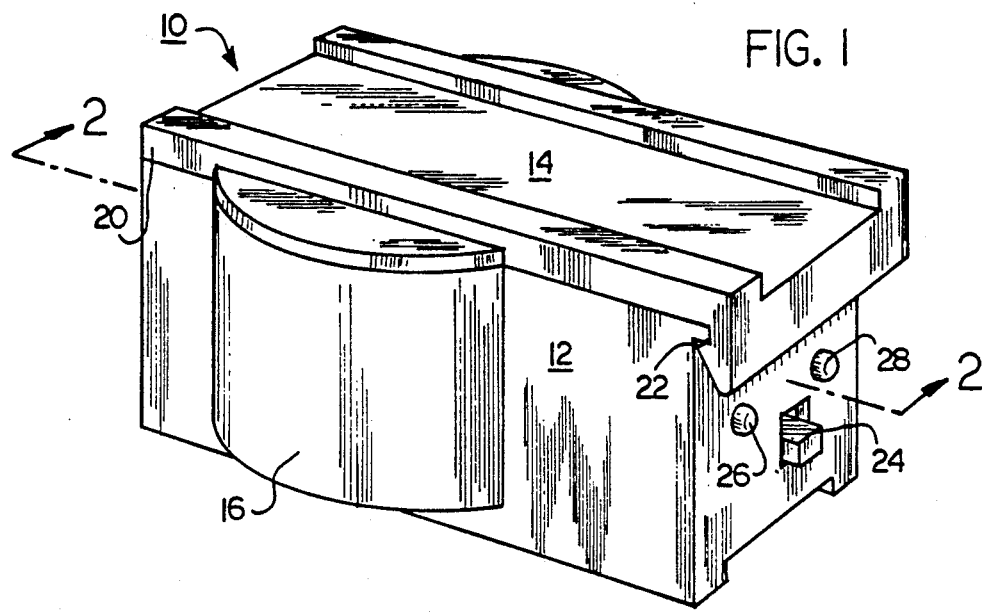
FIG. 1 is a perspective view of a tennis ball tester constructed according to the present invention.

Referring now to the drawings in general and FIG. 1 in particular, it will be understood that the illustrations are for the purpose of describing a preferred embodiment of the invention and are not intended to limit the invention thereto. As best seen in FIG. 1, a tennis ball tester, generally designated 10, is shown constructed according to the present invention. The tennis ball tester 10 includes three major sub-assemblies: a means for compressing the ball a fixed distance; a means for measuring the force on the compressed ball; and a means for producing an output signal indicative of the condition of the ball based on the force measured.

Tester 10 includes a lower housing 12 and upper housing 14. A test chamber 16 is defined within the lower housing 12. Upper housing 14 is attached to lower housing 12 by pivot means 20 located at one end of tester 10. Releasable latch means 22 connects the other end of upper housing 14 to lower housing 12. One end of lower housing 12 also includes an on/off switch 24 and indicator lights 26,28.

Figure 2:
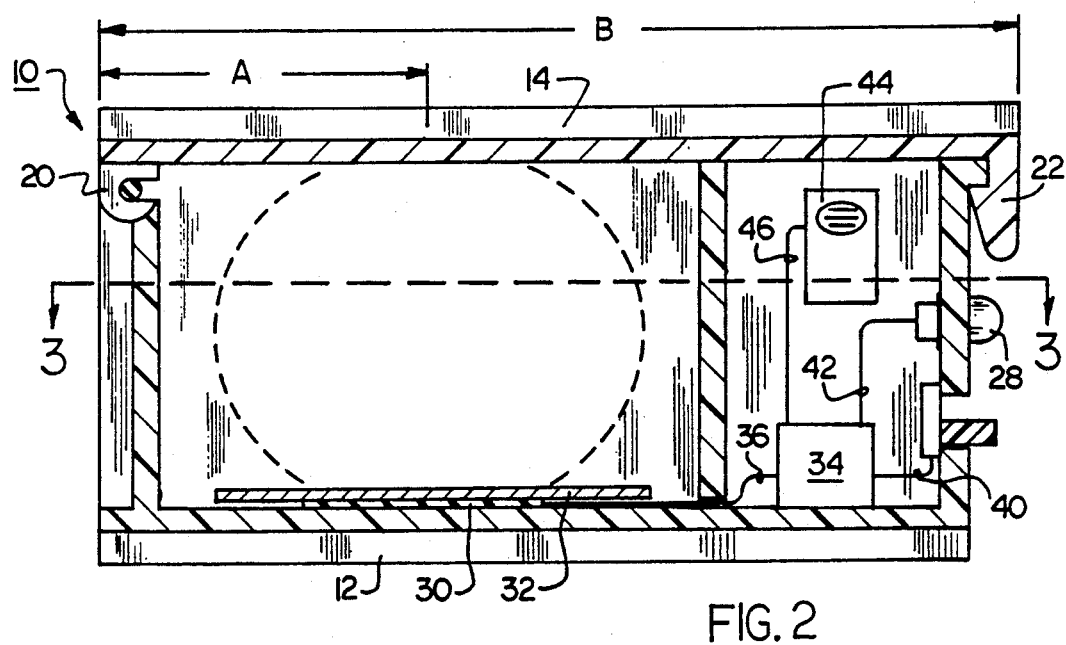
FIG. 2 is a sectional view of the device shown in FIG. 1, taken along lines 2—2.

As best seen is FIG. 2, dimension "A" corresponding to the distance between pivot point 20 and the contact point between the lower surface of the upper housing 14 and the ball (shown in dotted lines) is significantly less than dimension "B" corresponding to the distance between pivot point 20 and latch 22. This arrangement provides a significant mechanical advantage to the user when compressing the ball in test chamber 16 on the order of approximately 3:1. Since the test force is on the order of about 18 lbs., this arrangement allows the upper housing 14 to be secured to the lower housing 12 with only a force on the order of about 6 lbs. Such a small amount of required force allows even small children to operate the tennis ball tester 10.

As can also be seen in FIG. 2, sensor 30 is located on the upper surface of test chamber 16. Preferably, sensor 30 is a force sensing resistor of the type which is formed of a polymeric thick film which exhibits a decreasing resistance when increasing force is applied normal to its surface. Such devices are available from a number of suppliers, however, one device which has been found to be particularly suitable is available from Interlink Electronics of Santa Barbara, Calif.

Force sensing resistors are extremely durable devices and have a lifetime of greater than 10,000,000 actuators showing less than a 2% change in its resistance value. However, testing indicated that force sensing resistors cannot provide reliable readings of the force applied on the ball when used by alone. It was unexpectedly discovered that substantially uniform pressure is necessary to provide a reliable pressure reading by the sensor 30. Apparently, this is due to an unexpectedly uneven distribution of pressure between the surface of the ball and the surface of the sensor 30.

Thus, it was been found that it is necessary to provide a distributor plate 32 between the sensor 30 and the ball in order to provide reliable output from the sensor 30. Preferably, distributor plate 32 is a high durometer plastic sheet material having a thickness of approximately 1/16th of an inch. However, it is expected that other materials of various thicknesses could be adapted for use between the sensor 30 and the ball without undue experimentation.

A comparator module 34 is connected to sensor 30 by means of line 36. On/off switch 24 is connected to the comparator module by means of line 40. Output lines 42,43 are connected to LED indicators 26,28. In the preferred embodiment, an audio output 44 is included to supplement the LED indicators 26,28. The audio output 44 is connected to comparator module 34 by line 46. Details of the comparator module will be discussed below, however, it should be understood that the comparator module 34 may either be connected directly to a source of electrical power or may include a battery or other independent power source.

Figure 3:
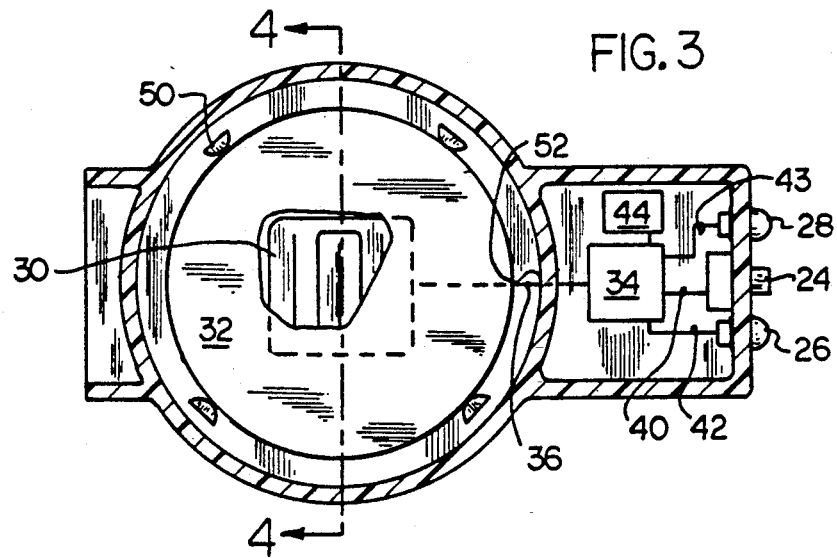
FIG. 3 is a sectional view of the device shown in FIG. 2, taken along lines 3—3.

The design of the test chamber 16 may be best understood by referring to FIG. 3. As can be seen, sensor 30 is located in the central portion of chamber 16 approximately equi-distance from the side walls of the chamber. Distributor plate 32 is located above sensor 30 and generally concentric with it. Tabs or adhesive could be used or clips 50 are used to secure distributor plate 32 in position. An aperture 52 in the wall of test chamber 16 allows line 36 to pass through and connect to comparator module 34. Since the comparator module and its related electronics are housed in a separate chamber from the test chamber 16, the second chamber may be filled with epoxy or otherwise sealed to provide reliable operation of the tester 10 even after exposure to severe weather.

Figure 4:
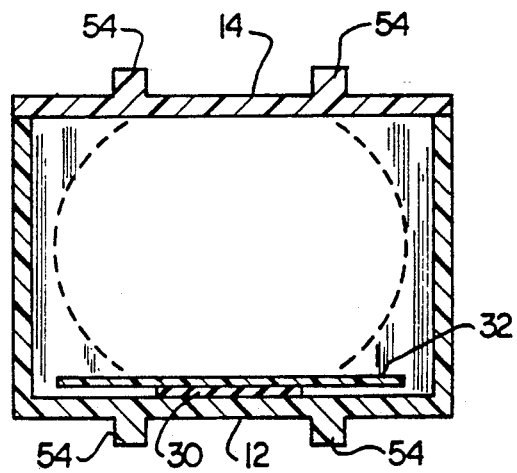
FIG. 4 is a sectional view of the device shown in FIG. 3, taken along lines 4—4.

Turning now to FIG. 4, it can be seen that the upper housing 14 and lower housing 12 include pairs of longitudinal extending ribs 54 to stiffen the surfaces of housings 12,14 in contact with the ball to be tested. While in the preferred embodiment only a single pair of ribs is used to reinforce each of the upper and lower housings, it should be understood that multiple pairs of ribs could be utilized if additional stiffness is needed.

Figure 5:
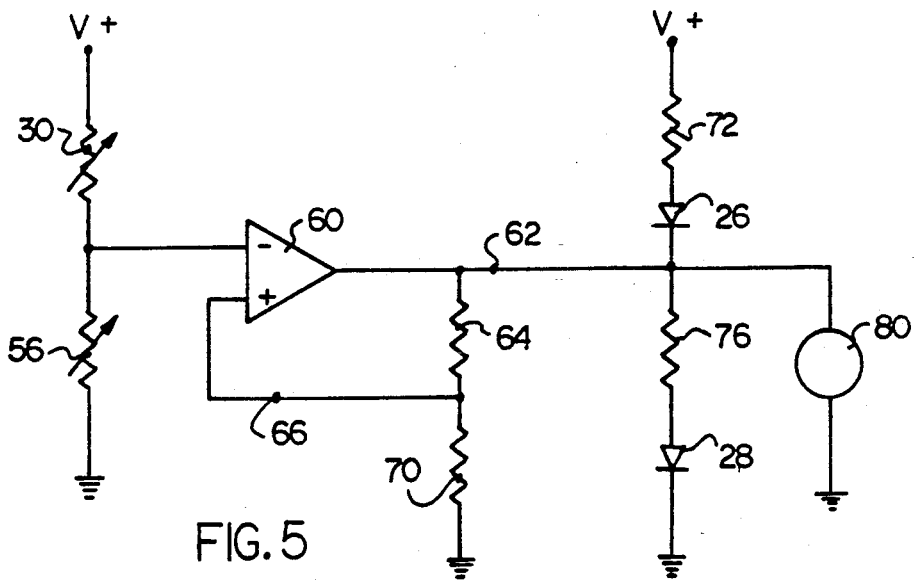
FIG. 5 is a schematic representation of the electrical circuit utilized by the present invention.

Finally, turning to FIG. 5, there is shown a schematic representation of the electrical circuit utilized by the present-invention. The force sensing resistor 30 is connected to a variable resistor 56 in a voltage divider configuration. Preferably, the range of this calibration resistor 56 is 0–2K. The input of operational amplifier 60 is connected between the force sensing resistor 30 and the calibration resistor 56. Preferably, an OP177 operational amplifier or equivalent is utilized.

A 150K resistor 64 is connected to the output 62 of operational amplifier 60 to provide feedback 66 to the amplifier. Resistor 64 controls the rise of the operational amplifier. A second resistor 70 having a value of 5K is connected to resistor 64 to provide hysteresis to the circuit, i.e., when the operational amplifier reaches a threshold level of output, it stays at that state, thereby preventing flicker of the LED indicator 28.

The output of the operational amplifier 60 is also connected to a node between a resistor 72, preferably a 1K resistor, LED 26, and resistor 76, also a 1K resistor, and LED 28. A buzzer 80 is preferably connected in parallel with resistor 76 and LED 78 to provide a supplemental audio indication of the playing condition of the ball.

In operation, with little or no load on the force sensing resistor 30, the output of the operational amplifier 60 goes "low" causing current to pass through LED 24. However, when force is applied to the force sensing resistor 30 by a ball in tester 10, the resistance of the sensor 30 decreases until the value falls below the threshold value, set by calibration resistor 56, corresponding to approximately 18 lbs. At that point, current flows through the operational amplifier 60 and through LED 28 indicating satisfactory condition of the ball.

Certain modifications and improvements will occur to those skilled in the art upon reading of the foregoing description. By way of example, the dimensions of test chamber 16 could be modified to test balls of various sizes and pressures. In addition, comparitor module 34 could be further modified to provide a digital display of the output of sensor 30. It should be understood that all such modifications and improvements have been deleted herein for the sake of conciseness and readability but are properly within the scope of the following claims.

I claim:

1. An apparatus for determining the playing condition of a tennis ball, said apparatus comprising:

(a) means for compressing said ball to a predetermined dimension, wherein said means for compressing said ball to a predetermined dimension includes a lower housing defining a test chamber for receiving the ball and an upper housing for compressing the ball in said test chamber, said upper housing being attached to said lower housing by pivot means located at one end of said lower housing and further including a releasable latch means located at the end of said upper housing further including a releasable latch means opposite said pivot means;

(b) sensor means for sensing the force exerted by said compressed ball and providing a signal representative of said force; and (c) means for receiving said signal representative of said force and comparing said signal to a predetermined value representative of a ball in good playing condition and providing an output signal representative of the condition of said ball.

2. The apparatus according to claim 1, wherein said sensor means is a polymeric thick film device which exhibits a decreasing resistance as increasing force is applied normal to the surface of said device and further including means located between said device and said ball for distributing the force exerted by said ball upon the surface of said sensor, thereby resulting in improved accuracy of said sensor means.

3. The apparatus according to claim 1, wherein said test chamber is located substantially adjacent to said pivot means and said upper housing extends beyond said test chamber, thereby enabling the ball to be compressed more easily.

4. The apparatus according to claim 3, wherein the ratio of the distance between said pivot means and the end of said upper housing opposite said pivot means and the distance between said pivot means and said test chamber is about 3:1.

5. The apparatus according to claim 1, wherein said lower housing defining said test chamber for receiving the ball and said upper housing for compressing the ball in said test chamber include longitudinally extending ribs for providing rigidity to said test chamber.

6. A sensor assembly for an apparatus for determining the playing condition of a tennis ball by compressing said ball to a predetermined dimension and measuring the force necessary to compress the ball to said predetermined position, said apparatus comprising:

(a) sensor means for sensing the force exerted by said compressed ball and providing a signal representative of said force, wherein said sensor means is a polymeric thick film device which exhibits a decreasing resistance as increasing force is applied normal to the surface of said device and further including means located between said device and said ball for distributing the force exerted by said ball upon the surface of said sensor, thereby resulting in improved accuracy of said sensor means; and (b) means for receiving said signal representative of said force and comparing said signal to a predetermined value representative of a ball in good playing condition and providing an output signal representative of the condition of said ball, wherein said means for receiving said signal representative of said force and comparing said signal to a predetermined value representative of a ball in good playing condition and providing an output signal representative of the condition of said ball is an operational amplifier having an input, an output and a feedback input and having its input connected between said sensor means and a variable resistor and further including a first resistor connected between the output of said amplifier and the feedback input of said amplifier for controlling the rise time of said amplifier and a second resistor connected between said first resistor and the feedback of said amplifier to provide hysterisis when the amplifier reaches a threshold level, thereby stabilizing the output of said amplifier.

7. An apparatus for determining the playing condition of a tennis ball, said apparatus comprising:
(a) means for compressing said ball to a predetermined dimension, wherein said means for compressing said ball to a predetermined dimension includes a lower housing defining a test chamber for receiving the ball and an upper housing for compressing the ball in said test chamber, said upper housing being attached to said lower housing by pivot means located at one end of said lower housing and further including a releasable latch means located at the end of said upper housing opposite said pivot means;
(b) sensor means for sensing the force exerted by said compressed ball and providing a signal representative of said force wherein said sensor means is a polymeric thick film device which exhibits a decreasing resistance as increasing force is applied normal to the surface of said device; and
(c) means for receiving said signal representative of said force and comparing said signal to a predetermined value representative of a ball in good playing condition and providing an output signal representative of the condition of said ball.

8. The apparatus according to claim 7, further including means located between said device and said ball for distributing the force exerted by said ball upon the surface of said sensor, thereby resulting in improved accuracy of said sensor means.

9. The apparatus according to claim 7, wherein said test chamber is located substantially adjacent to said pivot means and said upper housing extends beyond said test chamber, thereby enabling the ball to be compressed more easily.

10. The apparatus according to claim 9, wherein the ratio of the distance between said pivot means and the end of said upper housing opposite said pivot means and the distance between said pivot means and said test chamber is about 3:1.

11. The apparatus according to claim 7, wherein said lower housing defining said test chamber for receiving the ball and said upper housing for compressing the ball in said test chamber include longitudinally extending ribs for providing rigidity to said test chamber.

12. The apparatus according to claim 7, wherein said means for receiving said signal representative of said force and comparing said signal to a predetermined value representative of a ball in good playing condition and providing an output signal representative of the condition of said ball is an operational amplifier having an input, an output and a feedback input and having its input connected between said sensor means and a variable resistor.

13. The apparatus according to claim 12, further including a first resistor connected between the output of said amplifier and the feedback input of said amplifier for controlling the rise time of said amplifier and a second resistor connected between said first resistor and the feedback of said amplifier to provide hysterisis when the amplifier reaches a threshold level, thereby stabilizing the output of said amplifier.

* * * * *